| United States Patent [19] | [11] | 4,440,892 |
|---|---|---|
| Wolf et al. | [45] | Apr. 3, 1984 |

[54] AGENTS HAVING A TUMOR-INHIBITING ACTION AND THEIR USE

[75] Inventors: Gerhard D. Wolf, Dormagen; Bruno Bömer, Leverkusen; Robert Bierling, Wuppertal, all of Fed. Rep. of Germany

[73] Assignee: Bayer Aktiengesellschaft, Leverkusen, Fed. Rep. of Germany

[21] Appl. No.: 277,473

[22] Filed: Jun. 25, 1981

[30] Foreign Application Priority Data

Jul. 12, 1980 [DE] Fed. Rep. of Germany ....... 3026447

[51] Int. Cl.³ .......................... C08K 5/06; C08F 20/42
[52] U.S. Cl. ..................................... 524/283; 524/377; 524/804; 528/300; 568/594

[58] Field of Search ................ 424/305; 524/280, 283, 524/377, 401, 804, 812; 568/594, 595, 679; 528/300, 370

[56] References Cited

U.S. PATENT DOCUMENTS 3,248,414  4/1966  Stevens et al. ...................... 528/370
4,330,481  5/1982  Timberlake et al. ................ 528/370

*Primary Examiner*—Lorenzo B. Hayes
*Assistant Examiner*—Kriellion Morgan
*Attorney, Agent, or Firm*—Sprung, Horn, Kramer & Woods

[57] ABSTRACT

The invention relates to pharmaceutical compositions containing, as an active ingredient, a water-soluble polyester or polycarbonate based on one or more polyetherglycols of Formula (I) as defined in the specification. Also included in the invention is the use of said compositions for their tumor-inhibiting action.

2 Claims, No Drawings

AGENTS HAVING A TUMOR-INHIBITING ACTION AND THEIR USE

The present invention relates to the use of as agents having a tumour-inhibiting action of water-soluble polyesters or polycarbonates based on polyether-diols, which are in themselves known.

It has already been disclosed that complex $Cu^{II}$ and $Co^{II}$ salts of ethylene/maleic acid copolymers are active against Walker's sarcoma [see J. Med. Chem., 12 (1969), 1, 180].

Furthermore, polycations of various types, for example polyamidoamines, poly-N-morpholinoethylacrylamide and N-oxide polymers, have been tested for inhibition of the formation of metastases, with the result that only the dissemination of tumour cells, but not the growth of metastases in situ or metastases in a lymph node, could be influenced [see J. Med. Chem., 16 (1973), 496].

The activity of polymers with carboxyl groups against 180 sarcoma, as a function of the molecular weight, the charge density and also the metal-binding capacity of the carboxyl groups, has also been described [see Dissertation Abstr. Intern. B 33 (1973), 5,745].

Polyanions, for example poly-(ammonium acrylate), acrylic acid/acrylamide copolymers and also ethylene/maleic anhydride copolymers, are said to have, in connection with their tumour-inhibiting action, a heparin-like effect and also a virus inhibition, and moreover to increase the immunoreactions [see J. Med. Chem., 17 (1974), 1,335].

It is apparent from all this work that the tumour-inhibiting action of the polymers investigated hitherto against the experimental tumours used frequently only lies at the lower limit of significance and, in a number of cases, is restricted to prophylactic or adjuvant effects only. Disadvantageously, it is moreover apparent that the investigations cited were carried out in many cases on allogenic mouse tumours having a tendency towards spontaneous regression, and not systematically and under experimental arrangements relevant to clinical conditions.

Generally, there is a lack of data on the toxicity of the preparations, although the administration of high doses of substances having a molecular weight of more than 30,000 suggests inadequate elimination, or storage in the tissues.

W. Regelson et al. [see Nature, 186 (1960), 778–780] have investigated the tumour-inhibiting action of synthetic polyelectrolytes such as polyacrylic acid, polymethacrylic acid and hydrolysed or aminolysed ethylene/maleic anhydride copolymers. By comparing the actions of the dicarboxylic acid form, the amido-carboxylic acid form and the diamido form of ethylene/maleic anhydride copolymers, they found that at least one ionisable carboxyl group is necessary for a significant tumour inhibition. Experiments carried out by these authors with polyacrylamides in high doses (800 mg/kg, MW 60–70,000 and 400 mg/kg, MW 120,000) showed a negative tumour-inhibiting action or a non-significant positive action.

Likewise, agents having a tumour-inhibiting action have been described, which are characterised in that they contain at least one water-soluble homopolymer or copolymer which contains 1,3-dihydroxy-2-methylenepropane and/or derivatives thereof [see DOS (German Published Specification) 2,705,189]. Similar preparations with a similar action are water-soluble homopolymers or copolymers which contains 3,4-dihydroxybut-1-ene or hydroxyalkyl (meth)acrylates or derivatives thereof, or also derivatives of allyl alcohol, in polymerised or copolymerised form [see DOS (German Published Specification) 2,740,082].

Moreover, a certain tumour-inhibiting action of emulsifiers which contain incorporated polyethylene oxide chains has been disclosed. Thus, polyoxyethyleneated sorbitan monooleate ("Tween" 80-Trade Mark) has been used for immunisation against hyperdiploid Ehrlich's tumour [see Experientia, 29 (1973), 710].

A block copolymer of polypropylene oxide and polyethylene oxide ("Pluronic" F 68-Trade Mark) has proved to be active against the onset of metastases of Walker's 256 Ascites tumour, probably by influencing the blood coagulability [see Cancer, 29 (1972), 171]. As is known, these preparations are highly active emulsifiers and for this reason are not very well tolerated, in particular on parenteral administration.

It has now been found, surprisingly, that water-soluble polyesters and polycarbonates which have been prepared from polyether-glycols possess strong tumour-inhibiting properties or alleviate pain associated with tumour afflicted organisms.

In the molecular weight range from 1,000 to 100,000, the substances show statistically significant prophylactic and curative actions against solid tumours of syngenic systems, in a broad dosage range of 0.5 to 500 mg/kg, preferably 5 to 250 mg/kg, under experimental arrangements and methods of administration relevant to clinical conditions.

The acute toxicity of the purified substances is low; the LD 50 is generally above 2,500 mg/kg, for intravenous administration, so that the substances possess an unusually large therapeutic range.

The pharmaceutical compositions according to the invention incorporating such substances thus represent an important enrichment of therapy.

According to the present invention there are, therefore, provided pharmaceutical compositions containing as an active ingredient a water-soluble polyester or polycarbonate based on one or more polyether-glycols, which corresponds to the formula

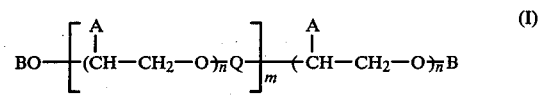

in which
A is statistically distributed hydrogen or methyl, 0.1%–50% preferably 0.1%–33% of the A groups being methyl,
the groups B are identical or different and are a hydrogen atom, an aliphatic, alicyclic or aromatic radical having up to 8 carbon atoms, (preferably a hydrogen atom or a $C_1$ to $C_4$ alkyl group), a group X—CO, X being a hydrogen atom or an aliphatic, alicyclic or aromatic radical (particularly mono- or bi-cyclic carbocyclic) having up to 7 carbon atoms (preferably a hydrogen atom or a $C_1$ to $C_3$ alkyl group), a group Y—O—CO—, Y being an aliphatic, alicyclic or aromatic radical having up to 7 carbon atoms (preferably a $C_1$ to $C_4$ alkyl group) or a group Z—NH—CO—, Z being a hydrogen atom or an aliphatic, alicyclic or aromatic radical having up to 7 carbon atoms (preferably a hydrogen atom or a $C_1$ to $C_4$ alkyl group), it being particularly preferred for one or both of the B groups to be hydrogen Q denotes a group

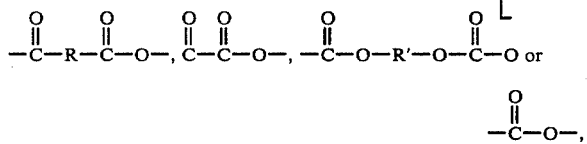

R being an alkylene or arylene having up to 20 carbon atoms (preferably up to 6 carbon atoms) and R' being alkylene having 2 to 18 carbon atoms (preferably 2 to 6 carbon atoms), n denotes a number from 5 to 500 (preferably from 8 to 300), and m denotes a number from 1 to 30 (preferably from 1 to 15).

As used herein and unless otherwise specified, (1) the term "alkyl" contains 1 to 7, preferably 1 to 3 carbon atoms, (2) the term "alicyclic" is preferably "cycloalkyl" containing 3 to 8, preferably 5 or 6 carbon atoms but may also represent "cycloalkenyl" or "cycloalkadi-nyl" containing 5 to 8, preferably 5 or 6 carbon atoms; and the term "aromatic" or "arylene" is preferably mono- or bi-cyclic carbocyclic aryl or arylene, respectively.

Preferred active ingredients for use in compositions of the present invention are those of the general formulae

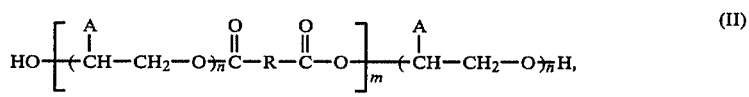

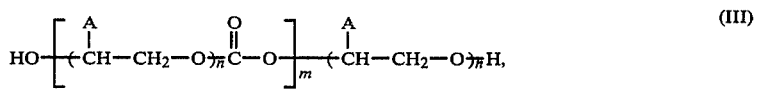

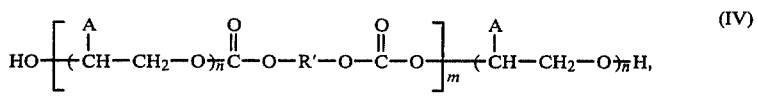

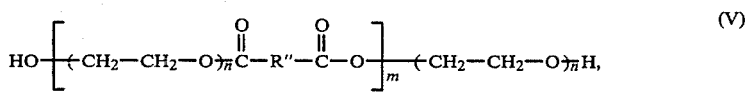

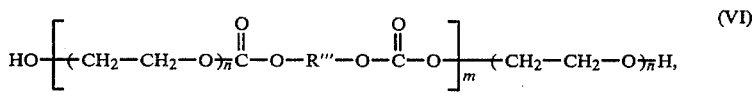

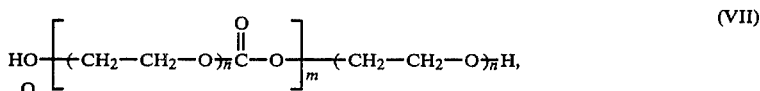

in which

A denotes statistically distributed H or $CH_{3L}$, 67 to 100 mol % being H and 0 to 33 mol % being $CH_3$, R denotes an alkylene or arylene group having up to 6 carbon atoms, R' denotes an alkylene group having 2 to 6 carbon atoms, R'' denotes an alkylene or arylene group having up to 6 carbon atoms, R''' denotes an alkylene group having 2 to 6 carbon atoms, n denotes a number from 8 to 300, and m denotes a number from 1 to 15.

The following compounds are examples of particularly preferred active ingredients in compositions according to the present invention:

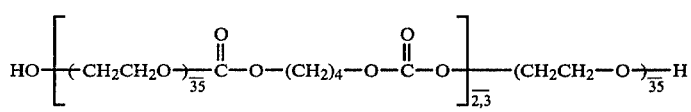

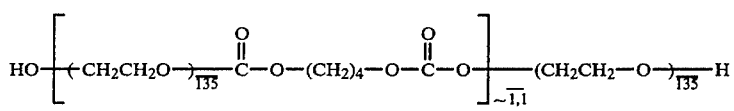

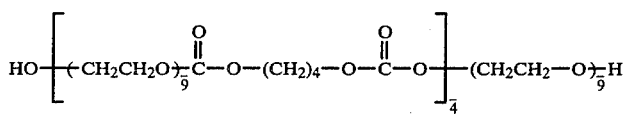

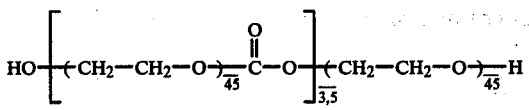

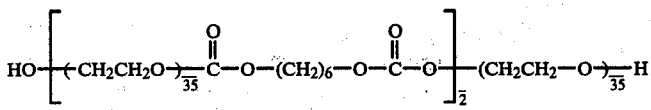

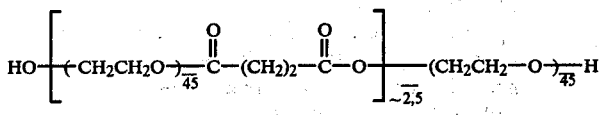

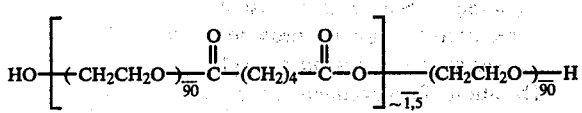

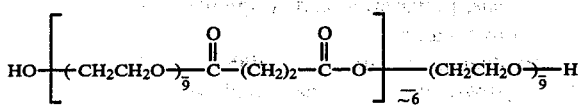

The polyesters to be used according to the invention can be prepared by known methods [see Houben-Weyl, Methoden der organischen Chemie (Methods of Organic Chemistry), 4th edition (1963), Volume 14/II, page 1 et seq.; Ullmanns Enzyklopädie der technischen Chemie (Ullman's Encyclopaedia of Chemical Technology), 3rd edition, Volume 14 (1963), pages 80–85].

The preparation by means of azeotropic condensation or by means of solution condensation is particularly preferred; in this process, a polyether-glycol and a dicarboxylic acid (particularly an alkane dicarboxylic acid, such as are used as the starting materials, the esterification is carried out in the presence of an acid catalyst and the water of reaction formed is distilled off azeotropically, for example with toluene. The degree of polymerisation "m" depends on the molar ratio of diol to dicarboxylic acid and on the extent of the reaction (degree of completion of the reaction). If the reaction is carried out with a molar excess of polyether-glycol, polyesters with predominantly OH end groups are obtained. Of course, apart from dicarboxylic acids, it is also possible to use dicarboxylic acid dichlorides and to react these with the polyether-glycols in the presence of tertiary amines.

The polycarbonates to be used according to the invention can be prepared either by phosgenation in an anhydrous medium, in the presence of an inert base, or by reaction of a bis-chloroformate of a low-molecular dihydroxy compound or of a polyether-glycol with a polyether-glycol, in the presence of an inert base [see Houben-Weyl, Methoden der organischen Chemie (Methods of Organic Chemistry), 4th edition, Volume 14/II (1963), pages 53 and 54]. In this case again, the degree of polycondensation "m" depends on the molar ratio of diol to phosgene or bis-chloroformate.

Of course, it is also possible to use mixtures of polyether-glycols of different average molecular weights or also mixtures of 2 or more dicarboxylic acids or of 2 or more bis-chloroformates, for the preparation of polyesters or polycarbonates to be used according to the invention.

The hydroxyl end groups of the polyesters or polycarbonates can be converted by known methods to ether groups, carboxylic acid ester groups, carbonic acid ester groups, or urethane groups. In the preparation of polyesters, ester end groups can be introduced by the concomitant use of corresponding amounts of a monocarboxylic acid, and in the case of the preparation of polycarbonates by the addition of a chloroformate of a monoalcohol.

The polyether-diols which are necessary for the preparation of the polyesters or polycarbonates to be used according to the invention are known to those skilled in the art. They are used in large amounts for the manufacture of polyurethane plastics. They are manufactured by the polymerisation or copolymerisation, with ring opening, of ethylene oxide and propylene oxide [see Houben-Weyl, Methoden der org. Chemic (Methods of Organic Chemistry), 4th edition, Volume XIV/2, 1963, page 427 et seq., Ullmanns Encyklopädie der technischen Chemie (Ullmann's Encyclopaedia of Chemical Technology), 3rd edition, Volume 14 (1963, pages 49–52)].

Copolymerisates of ethylene oxide and propylene oxide contain 0.1%–50%, preferably 0.1%–33% propylene oxide. Starting from ethylene oxide, the polyethylene glycols are obtained, which are very water-soluble from diethylene glycol up to products having molecular weights above $10^6$. Of the polypropylene glycols formed from propylene oxide, only the relatively low-molecular representatives are water-soluble. The solubility in water of the polypropylene glycols and of the ethylene oxide/propylene oxide copolymers can be improved by the incorporation of ionic groups. Ethylene oxide/propylene oxide random copolymers are water-soluble to a greater or lesser extent, depending on their molecular weight and content of propylene oxide units.

The agents according to the invention can be dissolved in physiologically isotonic sodium chloride solution, at temperatures of 20°–40° C., to give solutions of 0.5%–30% strength by weight. It is, however, possible to incorporate them into tablets, capsules and other preparation for the peroral administration. In addition to exceptionally low toxicity, they possess a strong tumour-inhibiting action against tumours in warm-blooded animals and are therefore intended for use in combating diseases caused by tumours.

As stated above, the invention also relates to the use in medicine as antitumorial agents of the compounds of the invention.

This invention further provides a method of combating the above-mentioned diseases in warm-blooded animals, which comprises administering to the animals a compound of the invention in admixture with an inert pharmaceutical carrier, e.g. a diluent. For parenteral administration such solutions should be sterile and, if appropriate blood isotonic.

It is envisaged that these active compounds will be administered parenterally (for example intramuscularly, intraperitoneally, subcutaneously and intravenously)-systemically or locally-preferably intraperitoneally, intravenously or intramuscularly. Preferred pharmaceutical compositions and medicaments are therefore those adapted for administration such as intraperitoneal; intravenous or intramuscular administration. Administration in the method of the invention is preferably intraperitoneal; intravenous or intramuscular administration. However, peroral administration can also be used.

In general it has proved advantageous to administer amounts of from 0.5 mg to 500 L mg/kg, preferably 5 mg to 250 mg/kg, of body weight per day to achieve effective results. Nevertheless, it can at times be necessary to deviate from those dosage rates, and in particular to do so as a function of the nature and body weight of the human or animal subject to be treated, the individual reaction of this subject to the treatment, the type of formulation in which the active ingredient is administered and the mode in which the administration is carried out, and the point in the progress of the disease or interval at which it is to be administered. Thus it may in some cases suffice to use less than the above-mentioned minimum dosage rate, whilst in other cases the upper limit mentioned must be exceeded to achieve the desired results. Where larger amounts are administered it can be advisable to divide these into several individual administrations over the course of the day.

The agents according to the invention are prepared by dissolving the active ingredients in physiological sodium chloride solution or by manufacturing tablets, capsules and other preparations for the peroral administration. The unusual breadth of the administration range mentioned above is a result of the unusual non-toxicity of the active ingredient.

The substances were tested for the induction of tumour inhibiting actions in numerous experiments, under various test conditions, against carcinoma EO 771 or against mouse sarcoma MCS 4.

The methodology of the investigations on both these experimental tumours can be seen from experiment descriptions (a) and (b).

DESCRIPTION OF EXPERIMENTS (A)

Tumour tests against carcinoma EO 771 on C 57 BL/6 mice

Animal strain:
C 57 BL/6 mice, inbred (SPF)

Methods:
Maintaining the tumor strain: 14–20 days after the last transplantation, subcutaneous inoculation of a suspension of cells of carcinoma EO 771 in 0.5 ml of 0.9% phosphate-buffered NaCl solution (PBS) into C 57 BL/6 mice.

Preparation of screening tests: Same procedure as in maintaining the strain of the tumour, but subcutaneous incoluation of a suspension of $5 \times 10^4$ tumour cells in 0.5 ml of 0.9% PBS.

Treatment: Single intramuscular injecttion of the required solution of substances 6 days prior to or 2 days after the tumour transplantation.

Duration of experiments: 18–22 days after the tumour transplantation. Thereafter, sacrificing of the animals, preparation and weighing of the subcutaneous tumours.

Evaluation parameters: Inhibition of the tumour growth by determination of the average tumour weight of control animals and groups of treated animals and calculation of the tumour weight (TW) index according to the formula:

$$TW \text{ index} = \frac{\emptyset \text{ tumour weight of the groups of 10 treated animals}}{\emptyset \text{ tumour weight of the control groups consisting of 10 animals}}$$

Assessment of the test results

TW index
0.8–0.6 = marginal activity
0.6–0.4 = moderate activity
<0.4 = good activity.

DESCRIPTION OF EXPERIMENTS (B)

Tumour tests against sarcoma MCS 4 on C 57 BL/6 mice

Maintaining the tumor strain: 10–14 days after the last transplantation, subcutaneous inoculation of a suspension of cells of sarcoma MCS 4 in 0.5 ml of 0.9% phosphate-buffered NaCl solution (PBS) into C 57 BL/6 mice.

Preparation of screening tests: Same procedure as in maintaining the strain of the tumour, but subcutaneous inoculation of a suspension of $2 \times 10^5$ tumour cells in 0.5 ml of 0.9% phosphate-buffered NaCl solution.

Treatment: Single intravenous injection of the required solution of substances 2 days prior to or 2 days after the tumour transplantation.

Duration of experiments: 18–22 days after the tumour transplantation. Thereafter, sacrificing of the animals, preparation and weighing of the tumours.

Evaluation and assessment of the results are carried out analogously to description of experiments (a).

TABLE 1

| | | Test results against carcinoma EO 771 | | |
|---|---|---|---|---|
| Compound No. | Dose mg/kg | Administration 1 × | Day of treatment* | Tumour weight index |
| I (Example 1) | 250 | intramuscular | −6 | 0.36 |
| | 250 | intramuscular | +2 | 0.38 |
| II (Example 2) | 50 | intramuscular | −6 | 0.39 |
| | 50 | intramuscular | +2 | 0.43 |
| III (Example 3) | 250 | intramuscular | −6 | 0.23 |
| | 250 | intramuscular | +2 | 0.42 |

*Days of treatment −6 = 6 days before tumour transplantation
+2 = 2 days after tumour transplantation

TABLE 2

| | | Test results against sarcoma MCS4 | | |
|---|---|---|---|---|
| Compound No. | Dose mg/kg | Administration 1 × | Day of treatment* | Tumour weight index |
| I (Example 1) | 0.5 | intravenous | −2 | 0.45 |
| | 5 | intravenous | +2 | 0.39 |
| III (Example 3) | 50 | intravenous | −2 | 0.24 |
| | 50 | intravenous | +2 | 0.32 |
| IV (Example 4) | 2.5 | intravenous | −2 | 0.37 |
| | 10 | intravenous | +2 | 0.32 |

*Day of treatment −2 = 2 days before tumour transplantation
+2 = 2 days after tumour transplantation The tumour weight indices of the preparations listed in Tables 1 and 2 show that the substances at various doses, for various methods of administration, and also on various days of treatment are capable of inducing distinct tumour-inhibiting activity both against carcinoma EO 771 and against sarcoma MCS4.

The following Examples illustrate the production of active ingredients used in the compositions of the present invention.

EXAMPLE 1

200 g of polyethylene glycol having an average molecular weight $\overline{M}_n$ of 1,550 were dissolved in 1 liter of toluene. For drying, 200 ml of toluene were distilled off under normal pressure. After cooling to room temperature, 20 g of dry pyridine were added, 20 g of butanediol bis-chloroformate were then added dropwise, whilst stirring, and the reaction mixture was subsequently stirred for 3 hours at room temperature. The pyridine hydrochloride was filtered off and washed thoroughly with toluene and the toluene solution was evaporated in vacuo on a rotary evaporator. The residue was recrystallised twice from 2:1 ethyl acetate/diethyl ether, rinsed with diethyl ether and dried in vacuo.

Yield: 180 g, $\overline{M}_n = 5,200$ (determined by membrane osmometry in DMF).

EXAMPLE 2

200 g of polyethylene glycol having a molecular weight $\overline{M}_n = 6,000$ were dissolved in 1 liter of toluene and dried by distilling off 200 ml of toluene. After cooling to room temperature, 4 g of dry pyridine were added and a solution of 3.6 g of butanediol bis-chloroformate in 50 ml of toluene was added dropwise. The reaction mixture was stirred overnight at room temperature. The batch was then diluted with 1 liter of toluene and stirred for a further 1 hour. After the pyridine hydrochloride had been separated off, the polycarbonate was then isolated as described in Example 1.

Yield: 185 g, $\overline{M}_n = 1.35 \times 10^4$ (determined by membrane osmometry in DMF).

EXAMPLE 3

200 g of polyethylene glycol having a molecular weight $\overline{M}_n = 2,000$, 8.85 g of succinic acid and 1 g of p-toluenesulphonic acid were dissolved in 500 ml of toluene. Toluene was distilled off at about 50 ml/hour, with the exclusion of moisture. As soon as 150 ml had distilled, 150 ml of absolute toluene were added. As soon as no more water passed over (after about 12 hours), the toluene was removed in vacuo on a rotary evaporator and the residue was recrystallised twice from 2:1 ethyl acetate/diethyl ether.

Yield: 177 g, $\overline{M}_n = 7,300$ (determined by membrane osmometry in DMF).

EXAMPLE 4

250 g of polyethylene glycol having a molecular weight $\overline{M}_n = 4,000$, 6.1 g of adipic acid and 1 g of p-toluenesulphonic acid were dissolved in 500 ml of toluene. Analogously to Example 3, toluene was distilled off for 24 hours and the polyester formed was purified by double recrystallisation.

Yield: 227 g, $\overline{M}_n = 10,500$ (determined by membrane osmometry in DMF).

What is claimed is:

1. A pharmaceutical composition containing as an active ingredient is a water-soluble polyester based on one or more polyether-glycols, corresponding to the formula

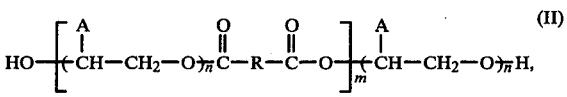

in which
A denotes statistically distributed hydrogen or methyl, 67 to 100 mol % being hydrogen atoms and 0–33 mol % being methyl groups,
R denotes an alkylene or arylene radical having up to 6 carbon atoms,
n denotes a number from 9 to 300 and
m denotes a number from 1 to 15.

2. A composition according to claim 1, in which the active ingredient is a water-soluble polyester based on one or more polyethylene glycols, corresponding to the formula
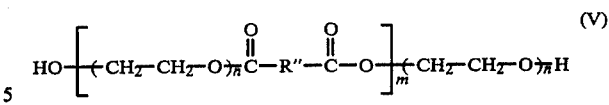
in which
n and m have the same meanings as in claim 1, and
R″ denotes alkylene or arylene having up to 6 carbon atoms.
* * * * *